United States Patent [19]

Magrini

[11] 4,153,048

[45] May 8, 1979

[54] THERMODILUTION CATHETER AND METHOD

[75] Inventor: Fabio Magrini, Milan, Italy

[73] Assignee: Cleveland Clinic Foundation, Cleveland, Ohio

[21] Appl. No.: 833,163

[22] Filed: Sep. 14, 1977

[51] Int. Cl.[2] A61B 5/02

[52] U.S. Cl. 128/692; 73/204

[58] Field of Search 128/2.05 F, 2.05 R, 128/2.05 V, 2 H; 73/204

[56] References Cited

U.S. PATENT DOCUMENTS

| | | | |
|---|---|---|---|
| 3,545,428 | 12/1970 | Webster, Jr. | 128/2.05 F |
| 3,726,269 | 4/1973 | Webster, Jr. | 128/2.05 F |
| 4,015,593 | 4/1977 | Elings et al. | 128/2.05 V |

*Primary Examiner*—Lee S. Cohen

*Attorney, Agent, or Firm*—Fay & Sharpe

[57] ABSTRACT

A new and improved pigtail type catheter and method particularly suited for the local thermodilution technique for determination of venous blood flow. The fluid injection aperture is disposed in the pigtail portion adjacent the most forward extending area thereof. A thermister is operably associated with the pigtail portion adjacent the distal end thereof intermediate the spaced apart side edges. A separate aperture may be conveniently included at the distal end of the pigtail portion to facilitate pressure readings of the venous flow. The new structural arrangement and method facilitate absolute thermal insulation between the fluid injected into the venous flow and the thermister, avoidance of contact between the thermister and vessel walls and a generally constant spacial relationship between the injection aperture and thermister.

13 Claims, 7 Drawing Figures

FIG. 1
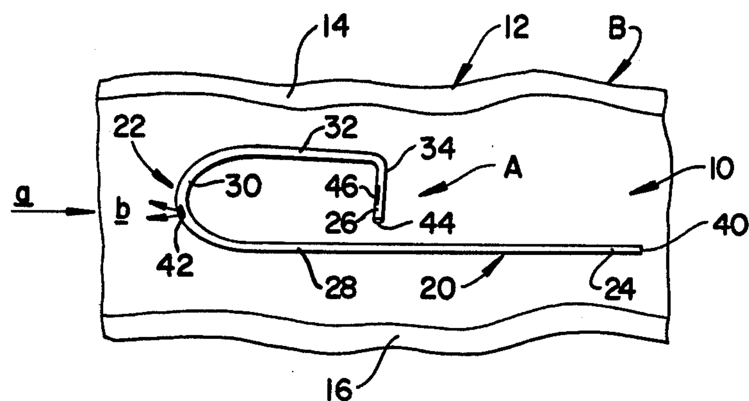
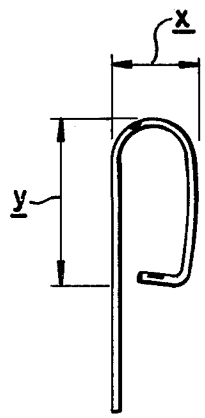
FIG. 2
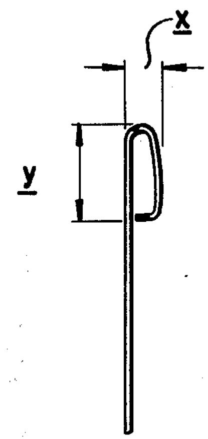
FIG. 3
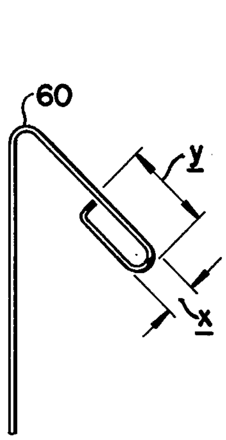
FIG. 4
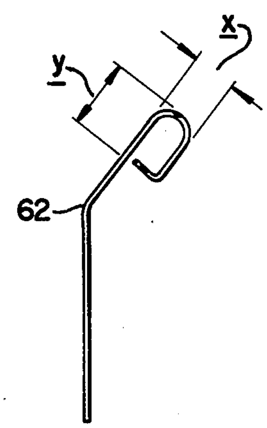
FIG. 5
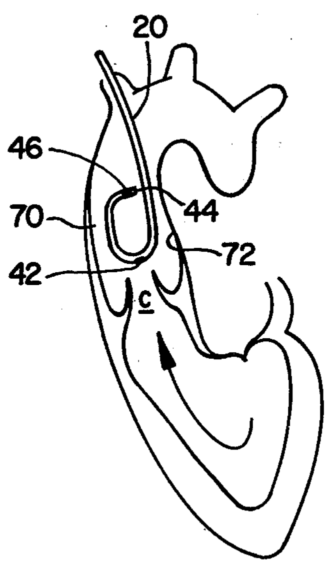
FIG. 6
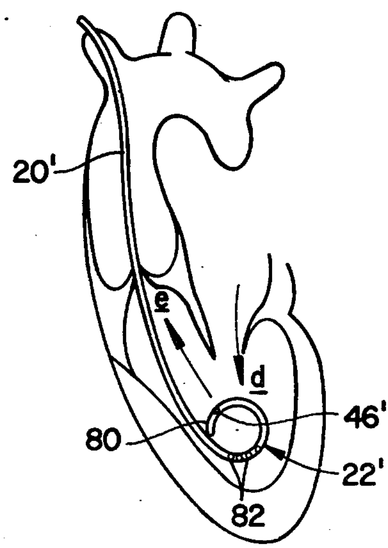
FIG. 7

THERMODILUTION CATHETER AND METHOD

BACKGROUND OF THE INVENTION

The invention pertains to the art of thermal dilution techniques and more particularly to the so called local thermodilution technique for determination of venous blood flow.

Venous blood outflow of several organs such as the heart, kidneys and brain have been variously measured by what is generally termed local thermal dilution techniques. All thermal methods for the study of circulation depend upon the induction of a change in the heat content of the blood stream. As a result of this change, a particular time dependent spacial distribution of temperature is developed in the blood according to the manner in which the change is brought about and as a function of the prevailing pattern of blood flow. Generally, thermal dilution refers to those techniques in which, following the artificial induction of a known change in the blood heat content at some point in the circulation, the resulting temperature change is followed at such a distance downstream that an even distribution of heat is presumed to have been developed over the whole vascular cross-section. Insofar as the specific technique with which the subject application is concerned, a catheter is employed to inject a mass into the blood stream which is miscible with and at a different temperature than the blood. This technique was first introduced in 1953 as a method for the measurement of volumetric blood flow rate and was termed thermodilution. Following initial introduction of the thermodilution technique on measurement of cardiac output, it was extended to the measurement of flow in single blood vessels in other parts of the body.

The so called thermodilution technique as just above generally described is now well known and widely used in the medical field. In practicing this technique, a wide variety of types and styles of catheters have been variously employed. Basically, these catheters include means for injecting the liquid injectate into the blood stream and means for sensing the temperature of the blood stream downstream of the point of injection. Such temperature sensing means may comprise either thermocouples or thermisters. In typical application, a charge of cold liquid is injected into the blood stream through the catheter in such a way as to produce intimate comixture following which the time course of temperature change is recorded through the thermocouple or thermister at a suitable point downstream in the blood flow. From this temperature-time curve and knowledge of the magnitude of the change in heat content of the blood produced by the injecting, the volume rate of flow can be calculated in a known manner.

The practicality of using the thermodilution technique insofar as its simplicity, the possibility of repeated measurements at short intervals and the use of a harmless indicator has been limited to a considerable extent by the complexity in construction of most thermodilution catheters heretofore available. Those catheter designs that were kept simple necessarily had to be of a large size and thus not suitable for many vessels. Moreover, all have shared certain undesirable characteristics which detracted somewhat from the validity of the results obtained in use.

That is, and in addition to the usual requirements such as adequate injectate mixing, negligible heat dispersion and adequate distance of the temperature sensing means from the injection site required to achieve acceptable results, two conditions related to the catheter itself must also be met. First, there must be absolute thermal insulation of the temperature sensing means with respect to the injectate and second, there must be a constant relative position between the injection and sensing sites with regard to the dynamics of flow and temperature changes in a vessel. These two requirements are deemed indispensible for accurate and reproducible determinations, the first because lack of insulation leads to unstable base line and distorted curves and the second because the geometry of heat dispersion influences the curves.

The importance of the above noted conditions is generally accepted and acknowledged by many investigators and the approaches heretofore suggested for meeting them have either been complex or unreliable. Prior catheter designs have included complex maneuvers utilizing umbrella catheters, separate wires and air insulation which have not proved to be particularly successful.

The present invention contemplates new and improved apparatus and method which overcome all of the above referred to problems and others to provide a new thermodilution catheter and method which are simple in design, easy to use, economical to use and which are readily adaptable to use in a number of different large and small blood vessels when practicing the local thermodilution technique.

BRIEF DESCRIPTION OF THE INVENTION

In accordance with the present invention, there is provided a new and improved pigtail type of catheter for practicing the thermodilution technique of measuring venous blood flow. The catheter comprises an elongated hollow catheter body having spaced apart first and distal ends. The catheter body has a pigtail portion which includes the distal end and is shaped to form a reversing loop-like area which extends back over the body toward the first end with at least the distal end extending generally back toward the body at or adjacent the pigtail portion thereof. A first lumen is included at the body first end for introduction of a fluid injectate into the catheter external of the venous flow and a first or injection aperture is provided in the pigtail portion to allow fluid injectate flow outwardly from the catheter into the venous flow. A temperature sensing means is operably associated with the catheter body intermediate the reversing loop-like area and the distal end and spaced from the first aperture for sensing a temperature change in the venous flow subsequent to injection of fluid injectate thereinto through the first or injection aperture.

In accordance with another aspect of the present invention, the catheter further includes a second aperture at the distal end of the body adapted for use in sensing pressure of the venous flow.

In accordance with still another aspect of the present invention, the body includes a generally straight section at least adjacent the loop-like area. The first aperture is disposed in the loop-like area at an angle in the range of no more than approximately 45° from this body straight section whereby the fluid injectate will be directed outwardly from the first aperture generally longitudinally into the venous flow.

In accordance with yet a further aspect of the present invention, the loop-like area defines a pig-tail plane with the body distal end being included therein. At least that portion of the body having the temperature sensing means associated therewith is configured to be disposed generally normal to the body straight section.

In accordance with yet another aspect of the present invention, there is provided a thermodilution method for monitoring venous blood flow by means of a pigtail type of catheter wherein the pigtail portion thereof comprises a reversing loop-like area at one end of an elongated hollow catheter body and terminating in a distal end with at least a portion of the loop-like area extending back toward the catheter body. The method comprises the steps of:

(a) positioning the catheter in the venous blood flow with the pigtail portion thereof disposed furthest upstream in the flow generally centrally thereof;

(b) injecting a fluid injectate having a temperature different than the blood flow into the catheter body at the other end thereof from the pigtail portion and exteriorly of the blood flow;

(c) allowing the fluid injectate to pass from the catheter pigtail portion into the blood flow upstream thereof through an injection aperture disposed between the area of merger of the pigtail portion and catheter body and the midpoint of the reversing loop-like area;

(d) locating at least a temperature sensing means on the catheter body adjacent the distal end thereof in the pigtail portion in a predetermined generally fixed spaced relationship from said injection aperture; and, (e) sensing a change in temperature of the venous blood flow at the temperature sensing means downstream of the point of injection of the injectate thereinto.

The principal object of the present invention is the provision of a new and improved thermodilution catheter and method which is simple in design and more accurate in use.

Another object of the present invention is the provision of a new and improved thermodilution catheter and method which are readily adaptable to use in local thermodilution applications for many single blood vessels.

BRIEF DESCRIPTION OF THE DRAWINGS

The invention may take physical form in certain parts and arrangements of parts, a preferred and alternative embodiments of which will be described in detail in this specification and illustrated in the accompanying drawings which form a part hereof and wherein:

FIG. 1 is a view of the subject new catheter design including a schematic showing of its placement in a blood vessel;

FIGS. 2–5 show various specific catheter designs which utilize the concepts of the subject invention for practicing local thermodilution techniques in specific blood vessels;

FIG. 6 shows one specific application of the subject thermodilution catheter and method; and, FIG. 7 shows yet another specific application of the subject thermodilution catheter and method wherein the catheter has a slighty modified pigtail configuration.

DESCRIPTION OF THE PREFERRED EMBODIMENT

Referring now to the drawings wherein the showings are for purposes of illustrating the preferred embodiment of the invention only and not for purposes of limiting same, the FIGS. show a catheter A operably disposed in a venous blood flow B which may comprise a vein, blood vessel, artery or the like.

More particularly and with specific reference to FIG. 1, venous blood flow B is through a generally channel or canal-like configuration 10 which comprises a vein, artery, blood vessel or the like having a continuous side wall 12 with opposed sides or surfaces 14,16. Blood flow through channel or canal 10 is in the direction a as shown in FIG. 1.

With continued reference to FIG. 1, catheter A comprises what is commonly referred to in the art and medical field as a pigtail type of catheter. The catheter is constructed from a material such as a suitable plastic or the like to have a hollow tube-like configuration and include an elongated body portion generally designated 20 with a pigtail portion generally designated 22. The material from which the catheter is constructed is such that once formed, it will generally retain its shape in order to desirably maintain a predetermined generally fixed relationship between at least some of the components. The reasons for this will become more readily apparent hereinafter. The catheter has a first end 24 and a distal end 26. Although not shown, it will be appreciated that first end 24 normally extends outwardly of channel 10 at the point of insertion of the catheter thereinto to receive the injectate or fluid which is to be injected into the venous flow itself. Disposed between body portion 20 and pigtail portion 22 is a generally straight catheter section generally designated 28. Pigtail portion 22 itself is comprised of a radiused or curvilinear section 30 forming a reversing loop-like area which then merges into a straight section 32 and then merges into a generally straight terminal end section 34 which includes distal end 26.

It should be noted that in the preferred arrangement of the invention here under discussion, straight section 28 and pigtail portion 22, as defined by sections 30,32 and 34, define a pigtail portion plane. Moreover, straight section 32 is generally parallel to straight section 28 and terminal end section 34 is disposed generally normal to straight section 28. With this particular arrangement, pigtail portion 22 defines a generally closed loop with distal end 26 disposed closely adjacent straight section 28.

A supply lument 40 is provided at first end 24 of the hollow catheter. Again, it will be appreciated to those skilled in the art that end 24 and supply lumen 40 are usually disposed outside venous flow B in practical application. A first or injection aperture 42 is disposed in the outermost wall of radiused or curvilinear section 30 to communicate with the hollow interior of the catheter and a second or pressure aperture 44 is disposed at distal end 26 to similarly communicate with the interior of the catheter. By way of specific example for a catheter A having the above noted configuration and used in the vena cava where curvilinear portion 30 has a radius of generally 1 cm, first or injection aperture 42 has a size of 0.6 mm. This size may, of course, be varied as deemed necessary and/or desirable to suit a particular use or vessel size. Moreover, the single first or injection aperture 42 may also be comprised of a plurality of apertures closely spaced to each other.

In the preferred arrangement here under discussion, the positioning of first or injection aperture 42 on radiused or curvilinear section 30 is deemed of some importance. More particularly, this aperture is disposed at an angle of between 30°–40° relative to the longitudinal axis of straight section 28 and, in no event, is this first aperture disposed beyond the midpoint of section 30.

The presence of second or pressure aperture 44 is not only adaptable for use in measuring pressure but also allows percutaneous introduction of the catheter into a blood vessel wherever desired. Percutaneous introduction itself, that is, performed through the skin, is accomplished by techniques well known in the medical field and need not, therefore, be discussed in greater detail herein.

In the preferred arrangement, a thermister 46 is mounted to pigtail portion 22 at terminal end section 34 spaced slightly inwardly therealong from distal end 26. In practicing thermodilution techniques, two types of temperature sensitive devices are suitable for measurement and recording of intravascular temperature. These comprise thermisters and thermocouples which are well known for application in this field of endeavor. Thermocouples, though simple to make, produce only a small electromotive force and must be used in low resistance circuits with sensitive galvanometers of long period unless suitable amplification can be arranged. Moreover, if an absolute measure of temperature is required, the reference junction of the thermocouple must be maintained at an accurately controlled temperature not varying by more than a few hundredths of a degree.

On the other hand, thermisters have a high negative temperature coefficient of resistance and an almost logarithmic temperature-resistance characteristic. Over a small range in temperature, this may be considered to be sufficiently linear but the characteristic can be made virtually linear over a much greater range and the sensitivity, though reduced, is adjusted to any convenient value by shunting the thermister with a fixed resistance of appropriate value. In the preferred embodiment, a thermister is employed. The specifics thereof do not themselves form a part of the invention as such termisters are of a commercially available type from, for example, Instrumentation Laboratories of Lexington, Mass. The thermister may be affixed to terminal end section 34 by convenient adhesive means and the connecting wire thereof may be conveniently passed through one of the catheter lumen or apertures outwardly of venous flow B toward the appropriate instrumentation connection.

In this environment, the thermister is used as one arm of either a Wheatstone bridge or a suitable alternating current bridge circuit. The current through the thermister must be kept small enough to produce no appreciable heating or the thermister will otherwise become sensitive to variations in blood flow rate and give spurious indications of temperature. The smaller the thermister, the more easily it can dissipate the heat it generates and, in addition, its thermal inertia to temperature changes decreases. Thus, the smaller the thermister the better will be its dynamic-response characteristics. The above discussion with regard to the preferred use of a thermister as temperature sensing means 46 as well as the alternative thermocouple arrangement is simply general in nature and is already known in the art, it being included here to merely provide further background information for the invention itself. Since the circuitry for the temperature sensing device does not form a specific part of the present invention, it too is not discussed in further detail herein. Such circuitry will be known to those skilled in the art and is commercially available as also from Instrumentation Laboratories of Lexington, Mass.

In use and with catheter A installed in venous blood flow B as shown in FIG. 1, a liquid injectate is passed through the hollow catheter from supply lumen 40. In the preferred use, this injectate comprises detrose at either room termperatue of 0° C., although other injectate fluids and temperatures could and are advantageously employed which do not depart from the overall intent or scope of the present invention. The injectate passes outwardly from the catheter at first or injection aperture 42 in the direction of arrow b into the venous blood flow and upstream of flow direction a thereof. Such injection may be either by the bolus (impulse input) or continuous infusion methods as is known.

As will be noted in FIG. 1, entry of the injectate into the blood flow in direction b will be generally centrally of channel 10 so that as it is thereafter carried downstream by the blood flow, injectate dispersion through the blood will be substantially even. Introduction of the injectate and its subsequent dispersion changes the blood temperature at the point of injection and this change is monitored as the dispersed injectate passes by and in contact with temperature sensing means or thermister 46. This change in temperature is transmitted through the thermister wire to outside venous blood flow B whereby the blood flow rates may then be calculated in conventional and known manners. As these calculations are known and do not form a specific part of the present invention, further discussion thereon is not deemed necessary herein.

The particular advantages obtained in using the catheter configuration shown in FIG. 1 and described hereinabove in detail is that thermal coupling is avoided between thermister 46 and the injectate as it passes from supply lumen 40 to and outwardly from first or injection aperture 42. The importance of such thermal insulation is well recognized in the medical field but the problem has never before been satisfactorily resolved. Such importance is deemed to be fully demonstrated by the many attempts made by other prior systems which have included complex maneuvers utilizing umbrella catheters, separate wires and air insulation. None of these prior efforts have, however, proved successful and the subject catheter is constructed to provide absolute thermal insulation between the injectate and thermister since the injectate passes outwardly from the catheter through first or injection lumen 42 prior to the time it can reach or come into communication with terminal end section 34 on which thermister 46 is mounted.

A further important feature of the present invention is that it overcomes another source of error in prior catheters employed for practicing the thermodilution technique for determining venous blood flow is that the thermister is located in such a manner that it cannot contact side wall 12 of channel or canal 10. Occurance of such contact leads to alterations of the dilution curve which, if not properly monitored, can lead to significant errors in estimating blood flow. Further, and even though the catheter tips of prior designs may only transiently touch the vessel walls, this transient touching may lead to errors in estimating blood flow without causing any obvious distortion of the record. While the prior umbrella type of catheter avoids this latter problem, substantial difficulties are encountered when using it to catheterize smaller vessels. The structure and configuration of the subject catheter, however, provides a constant position of the thermister in generally the center of the blood stream without sacrificing ease of catheterization of small vessels.

Finally, the subject new catheter design is such that a relatively constant and precise distance between first or injection aperture 42 and thermister 46 may be maintained. Since catheter A is constructed from stainless steel, plastic or the like, pigtail portion 22 thereof may have a self supporting and relatively stable configuration. Prior catheters used in practicing the thermodilution technique of measuring blood flow have had the temperature sensing means variously affixed thereto. Many times, this affixing was in such a manner that there could be relative spacial repositioning and variations between the point of injection of the injectate and temperature sensing means thus affecting the validity of the blood flow data obtained.

The requirements that (1) there be absolute thermal insulation of the thermister and (2) there be a constant relative position between the injection and sampling sites are recognized as being indispensible for obtaining accurate and reproducible blood flow determinations. The first requirement is important because lack of insulation leads to unstable baseline and distorted curves. The second requirement is important because the geometry of heat dispersion influences the curve.

The concepts of the subject invention are adapted to many different and specific applications within the body as is shown in, for example, FIGS. 2–5. FIG. 2 shows catheter arrangement for use in the vena cava, FIG. 3 shows a catheter arrangement for use in the jugular and femoral veins, FIG. 4 shows a catheter arrangement for use in the renal vein and FIG. 5 shows a catheter arrangement for use in the coronary sinus. The overall arrangements insofar as the loop-like configuration of the pigtail portion for each of these alternatives are substantially identical to that shown and described hereinabove with reference to FIG. 1.

The primary differences here are simply in dimensioning due to the size of the vessel in which the catheter is to be inserted. The x dimension on each of these alternatives represents the distance between the opposed sides of the pigtail portion or generally the diameter of the curvilinear portion thereof and the y dimension generally represents the distance between the outermost extending area of the pigtail portion and the thermister. the FIG. 2 x dimension is approximately 2 cm. and the y dimension is approximately 4 cm.; in the FIG. 3 arrangement, the x dimension is approximately 0.5 cm and the y dimension is approximately 2 cm; in the FIG. 4 arrangement, the x dimension is approximately 0.5 cm and the y dimension is approximately 2 cm; and, in the FIG. 5 arrangement, the x dimension is approximately 1 cm and the y dimension is approximately 1.5 cm. The showings of these alternative configurations are simply for purposes of demonstrating other specific applications of the subject inventive concepts which are used substantially as described in detail above with reference to FIG. 1. It will be noted that the FIGS. 4 and 5 arrangement include bends 60,62, respectively, in the body portions. These bends are simply to accommodate the specific vessel configurations involved.

The concepts of the subject invention are equally applicable to other vessels having larger or smaller sizes. The distance between the injection site at the injection aperture and the thermister itself may be varied to accommodate local conditions such as the length of the vessel and the presence of collateral branches. Moreover, the radius of the pigtail portion and the shape of the catheter can be easily formed to accommodate the specific vessels to be investigated as shown, for example, in FIGS. 2–5. For particularly small vessels, the size of the pigtail or tip may be as small as a #3 French, that is, 1 mm or 0.039". When made this small, no second or pressure aperture 44 is included in the distal end of the catheter for accommodating a transducer to monitor pressure.

FIG. 6 shows use of the catheter specifically described with reference to FIG. 1 as employed to measure left ventricular outflow in the heart. In this instance, the catheter is disposed between side walls 70,72 and functions to monitor blood flow in direction c in the same manner hereinabove described in detail.

FIG. 7 shows a slight modification in the catheter itself and its use for ventricular volume monitoring. In FIG. 7, like numerals are employed to identify like components with the inclusion of a primed (') suffix and new numerals are employed to identify new components. here, pigtail portion 22' has a generally circular configuration with terminal end section 80 which includes thermister 46' being generally curved instead of generally straight as shown in FIG. 6. Also, the single first or injection aperture has been replaced by a plurality of closely spaced smaller injection apertures 82. Here, the catheter is employed to measure volume of blood flow entering from a direction d and then exiting in a direction e at an angle of generally 30° spaced from blood flow d. Other than the structural differences specifically noted, use and operation of the catheter shown in FIG. 7 is identical with that hereinabove previously described.

The invention has been described with reference to the preferred and alternative embodiments. Obviously, modifications and alterations will occur to others upon the reading and understanding of this specification. It is my intention to include all modifications and alterations insofar as they come with the scope of the appended claims or the equivalents thereof.

Having thus described my invention, I now claim:

1. A pigtail type of catheter for practicing the thermodilution technique of measuring venous blood flow, said catheter comprising:

an elongated hollow catheter body having spaced apart first and distal ends, said body merging into a pigtail portion including said distal end and forming a reversing loop-like area extending back over said body toward said first end with at least said distal end extending generally back toward said body adjacent the area of merger thereof with said pigtail portion; a supply lumen at said first end for introduction of a fluid injectate into said hollow catheter body and a first aperture in said pigtail portion communicating with the hollow interior of said catheter body to allow fluid injectate flow outwardly of said catheter into said venous flow; and, temperature sensing means operably associated with said pigtail portion spaced therealong toward said distal end from said first aperture for sensing a temperature change in said venous flow after said fluid injectate has been injected thereinto through said first aperture.

2. The catheter as defined in claim 1 further including a second aperture at the body distal end communicating with the hollow interior of said catheter body.

3. The catheter as defined in claim 1 wherein said body includes a generally straight section at least adjacent the area of merger between said body and pigtail portion, said first aperture being disposed in said reversing loop-like area at an angle of no more than approximately 45° from said straight section whereby said fluid injectate will be directed outwardly from said first aperture into said venous flow.

4. The catheter as defined in claim 3 wherein said angle is in the range of approximately 30°–40°.

5. The catheter as defined in claim 1 wherein said reversing loop-like area has a generally arcuate configuration at least at the area thereof which reversely bends back toward said body.

6. The catheter as defined in claim 1 wherein said reversing loop-like area defines a pigtail portion plane with said distal end being in said plane and at least that portion of said pigtail portion having said temperature sensing means associated therewith being disposed generally normal to said body.

7. The catheter as defined in claim 6 wherein said reversing loop-like area is substantially closed with said distal end closely spaced to said body.

8. In a pigtail type catheter of the type employed to measure venous flow wherein said catheter includes a hollow elongated body having first and distal ends and which body merges into a pigtail portion adjacent said distal end which is inserted into communication with said venous flow, said pigtail portion generally forming a reversing loop-like area which extends back around said body and wherein a fluid injectate is introduced into said catheter from said first end and thence into said venous flow from at least one injection aperture spaced along said catheter from said first end in fluid communication with the hollow interior of said body in order that a temperature change in said venous flow may thereafter be monitored downstream thereof, the improvement comprising:

a portion of the pigtail portion including said distal end extending back toward said body adjacent the area of merger between said body and pigtail portion; and, temperature sensing means operably mounted on said portion of said pigtail portion toward said distal end from said at least one injection aperture for sensing a temperature change in said venous flow following injection of said fluid injectate thereinto through said at least one injection aperture.

9. The improvement as defined in claim 8 wherein said at least one injection aperture is disposed in said pigtail portion to facilitate fluid injectate flow outwardly thereof generally axially of said venous flow, said at least one injection aperture being disposed in said pigtail portion at an angle of no more than 45° as measured from a generally straight section of said body adjacent the area of merger between said body and pigtail portion.

10. The improvement as defined in claim 9 wherein the angle is in the range of between approximately 30°–40°.

11. The improvement as defined in claim 10 wherein said distal end is closely spaced to said body portion and includes a second aperture communicating with the hollow interior of said body.

12. A thermodilution method for monitoring venous blood flow through use of a pigtail type catheter wherein the pigtail portion thereof comprises a reversing loop-like area at one end of an elongated hollow catheter body and which pigtail portion terminates in a distal end with at least a portion of said loop-like area extending back toward said catheter body, said method comprising the steps of:

positioning the catheter in said venous flow with said pigtail portion disposed furthest upstream of said flow and generally centrally thereof;

injecting a fluid injectate having a temperature different from that of said venous flow into said hollow catheter body at the other end thereof from said pigtail portion;

allowing said fluid injectate to pass from said catheter pigtail portion into said venous flow generally upstream thereof through an injection aperture communicating with the hollow interior of said catheter body between the area of merger of said pigtail portion and body and the midpoint of said reversing loop-like area;

locating at least a temperature sensing means on said body spaced from said injection aperture toward the distal end thereof in said pigtail portion and between the side edges of said pigtail portion in a predetermined generally fixed spaced relationship from said injection aperture; and, sensing a change in temperature of said venous flow at the temperature sensing means downstream of the point of the injection of said fluid injectate thereinto.

13. The method as defined in claim 12 further including the steps of providing a pressure sensing aperture at said distal end in said pigtail portion communicating with the hollow interior of said catheter body and sensing pressure of said venous flow at said pressure sensing aperture.

* * * * *